May 26, 1942. A. W. WAHL Plant Pat. 520
PEACH TREE
Filed Dec. 8, 1939
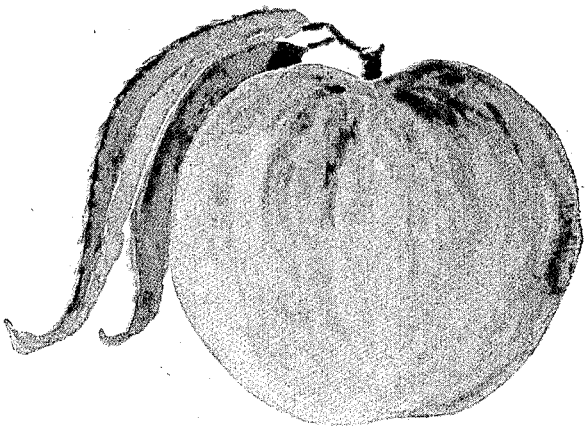
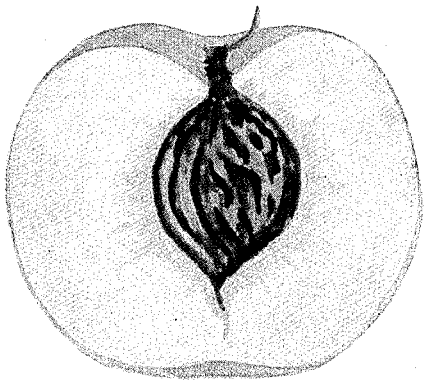
Inventor
Albert W Wahl Patented May 26, 1942

UNITED STATES PATENT OFFICE

520

PEACH TREE

Albert W. Wahl, Clarkston, Wash., assignor to H. Lynn Tuttle, Clarkston, Wash.

Application December 8, 1939, Serial No. 308,197

1 Claim. (Cl. 47—62)

This peach tree, obviously a seedling, was, when discovered, growing in a fence-row in front of my house. The fence was later removed. The tree bore its first fruit in 1921. The fruit was large, well colored and of good quality so I decided to leave the tree there. Its exceptional hardiness was soon apparent for it cropped regularly every year whereas other varieties failed. It has cropped each year since it first bore fruit in the year 1921 altho, due to severe winters and/or spring freezes, such common varieties as Elberta and J. H. Hale have failed from one-half to two-thirds of the time. Several times during the past 18 years it has been the only peach variety on or near my place to bear fruit, withstanding winter temperatures as low at 23 degrees below zero. It has the characteristic of blooming from small underdeveloped buds in case the first and larger buds are injured. It also tends to early dormancy in the fall and this characteristic doubtless puts the buds and wood in good condition to withstand the early winter freezes. The tree itself has never shown any sign of winter injury.

Among other characteristics I noted was the tenacity with which the fruit adhered to the tree. There has never been any loss from falling even when the fruit was left hanging for periods as long as two weeks after ripening. As a test in the season of 1927 I left a limb loaded with peaches for a period of two weeks after the rest were picked. There was no loss whatsoever from falling and the peaches were still in excellent condition for local market.

Another outstanding characteristic of my peach is that it shows relatively little effect from cuts and bruises. It does not rot or discolor readily. Quite severe bruises do not show on the skin surface or discolor the flesh. The skin does not loosen.

Also, whether thinned or unthinned, the peaches of this variety always attain good commercial size. Even when left hanging so close they touch each other they are always sufficiently large for good commercial usage. They also grow very uniform in size, shape, color and quality, producing a very high percentage of good fruit. Fruit production is very abundant, however fruit tends to develop along the limb rather than in clusters as is found in some varieties.

The tree is entirely self-fertile. It has produced good crops with no other peach trees near and also in years when fruit buds on all other peach trees were killed by winter freezes and did not bloom at all.

The fruit colors highly, well in advance of picking season.

The tree blooms freely. In size and color the bloom resembles that of the Rochester and Rio Oso Gem peach varieties. The period of bloom is longer than most peach varieties, usually about 28 days. This is apparently due to small blossom buds developing and is especially noticeable and valuable when early bloom is caught by a freeze in its tender stage.

Ripening season here is normally 14 to 18 days ahead of standard Elberta and 8–10 days after Golden Jubilee varieties.

The following description follows the outline suggested in the Book, "Systematic Pomology" by U. P. Hedrick published 1925:

Tree: Medium to large, vigorous, upright to spreading, dense, round-topped, hardy, very productive, regular bearer.

*Trunk.*—Fairly heavy, quite smooth.

*Branches.*—Medium to slender, smooth, green to red in the fall, glossy, older branches grey-green.

*Lenticels.*—Inconspicuous.

*Leaves.*—Length 6¾", with 1¾", large, lanceolate, acutely pointed, medium thick, dark green on top grey green below, smooth, waved and folded. *Leaf margin*—few glands, finely serrate. *Petiole*—short, thick. *Glands*—average number 2, many glandless, usually opposite, small globose, green during rapid growth, on stem or edge of leaf near stem.

*Flower buds.*—Hardy, rather small, dark brown, obtuse to conic, free, pubescent.

*Flowers.*—Date of bloom Apr. 1 to 28, rather early over long period, very large, pink, fertile, produce pollen.

Fruit: Early midseason, ripens Aug. 12 here, keeping quality, good; shipping quality, good; length 2⅞", width 3", large, regular, roundish oblate, halves equal to slightly unequal. *Cavity*—deep, narrow, regular, somewhat flaring. Suture shallow but distinct. *Apex*—almost no tip, depressed. *Color*—yellow, striped and mottled with deep red.

*Pubescence.*—Short, thin. *Skin*—thick, medium tough, adherent.

*Flesh.*—Golden to orange yellow, red around pit, juicy, fine grained, very firm, sweet to subacid, sprightly, aromatic. *Quality*—very good to best.

*Stone.*—Free, roundish, flattened toward stem end and along ventral side, abruptly pointed and point very short, finely corrugated and deeply pitted, red to brown. *Use*—dessert, kitchen, shipping market.

*Remarks.*—Ripens thru a good picking season, colors before ripe, bears very young.

By reproduction thru budding I now have 15 trees that have been bearing since 1935. They have the same characteristics of tree, fruit and hardiness as has the original tree.

This variety is of important commercial value because:

(1) The extreme hardiness of the tree helps eliminate crop losses.

(2) The fruit adheres to the tree both before and after ripening.

(3) The fruit keeps well on the tree for a considerable period after ripening with little deterioration. This lessens loss of fruit and permits economy and convenience in picking.

(4) Due to a rather tough skin that adheres to the flesh and to a good texture of flesh the fruit is resistant to bleeding following cuts and bruises. This eliminates much loss in handling.

(5) The fruit being well rounded and slightly depressed at the apex facilitates packing.

(6) The fruit is always very uniform in size, shape, color and quality. There is very little cullage.

(7) Each peach tends to develop to a good commercial size regardless of whether it is thinned or unthinned. This is true even when crowding all along the limbs.

(8) The color is always good, the fruit coloring well before ripening.

I claim:

A new and distinct variety of peach tree, as herein described, characterized by its exceptional hardiness and productivity, the tenacious adherence of the fruit to the tree, the keeping qualities of the fruit and its resistance to rotting or discoloration from bruises, the desirable shape of the fruit and its uniformity in size, shape and color, the rather long period of bloom and the tendency to early dormancy as associated with hardiness and productivity.

ALBERT W. WAHL.